United States Patent [19]

Howe et al.

[11] Patent Number: 4,872,917
[45] Date of Patent: Oct. 10, 1989

[54] SCLARAI ALKYL ETHERS AND SMOKING COMPOSITIONS CONTAINING A SCLARAL ALKYL ETHER FLAVORANT

[75] Inventors: Charles R. Howe; Everett W. Southwick, both of Richmond; Richard H. Cox, Midlothian, all of Va.

[73] Assignee: Philip Morris Incorporated, New York, N.Y.

[21] Appl. No.: 818,452

[22] Filed: Jan. 13, 1986

[51] Int. Cl.[4] .................................................. A74B 3/12
[52] U.S. Cl. .................................... 131/275; 131/276; 131/277
[58] Field of Search ................ 131/275, 276, 277, 278

Primary Examiner—V. Millin

[57] ABSTRACT

This invention provides novel sclaral alkyl ether compounds, and smoking compositions which contain a sclaral alkyl ether compound as a flavorant additive.

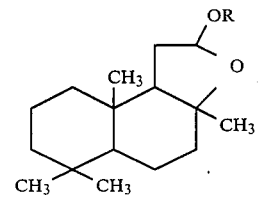

Under cigarette smoking conditions the sclaral ether is a volatile component which enhances the flavor of the mainstream smoke and the aroma of sidestream smoke.

13 Claims, No Drawings

SCLARAI ALKYL ETHERS AND SMOKING COMPOSITIONS CONTAINING A SCLARAL ALKYL ETHER FLAVORANT

BACKGROUND OF THE INVENTION

Domestic tobaccos such as burley, Maryland, flue-cured, bright leaf and Virginia tobaccos have less perceived flavor and aroma under smoking conditions than the Oriental or aromatic tobaccos which are imported into the United States from regions such as Turkey, Greece, Bulgaria and Abinol is a di-unsaturated labdanoid diterpene alcohol which is found in the cuticular wax of the Oriental type of tobacco leaf:

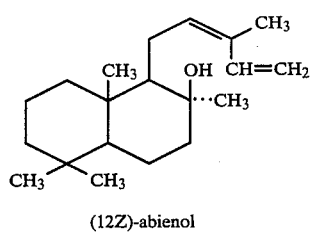

(12Z)-abienol

Oriental green leaf contains abienol, but there is no evidence of abienol after the leaf is sun-cured. Tobacco trichomes are the source of the abienol, and there is a thin film of abienol on the green leaf which is exposed to sunlight and air during curing. It appears that abienol is converted by photo-oxidative degradation, and generates the derivatives which provide the characteristic woody note of Oriental tobacco.

I. Wahlberg et al., in Acta Chem. Scand., B32, 203(1978) and B33, 437(1979) describe the chemistry of abienol photo-oxidation. Many of the photo-oxidation products obtained were identical to those found in sun-cured Oriental tobacco.

Among the abienol-derived constituents of sun-cured Oriental tobacco is sclareclide (norambreinolide)(I), which is structurally related to sclaral(II):

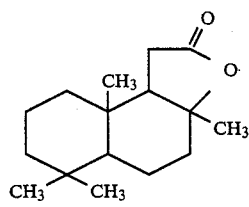

I.

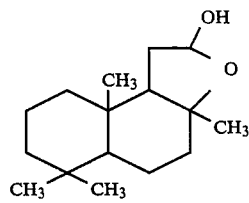

II.

U.S. Pat. No. 2,978,365 describes domestic tobacco compositions which contain sclaral as a flavorant additive. The additive imparts a cedar-like flavor and aroma to the main stream and side stream smoke of tobacco products under smoking conditions.

There is continuing interest in the development of improved low delivery smoking compositions which generate mainstream smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking tobacco compositions having incorporated therein a flavorant composition which under normal smoking conditions imparts an improved flavor to mainstream smoke and an improved aroma to sidestream smoke.

It is a further object of this invention to provide novel abienol-related compounds which are adapted to be incorporated into tobacco compositions, and which under normal smoking conditions are released as volatile flavorants into cigarette smoke.

Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001 and 2 weight percent, based on the total weight of filler, of a sclaral ether flavorant additive corresponding to the formula:

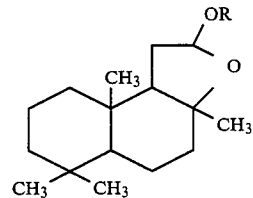

where R is an alkyl group containing between about 1–4 carbon atoms.

Illustrative of $C_1$–$C_4$ alkyl groups are methyl, ethyl, 2-methoxyethyl, propyl, isopropyl, butyl, isobutyl, and t-butyl radicals.

The formal nomenclature for the formula represented above is 2-alkoxy-3a,6,6,9a-tetramethyldodecahydronaphtho-[2,1-b]furan.

When a present invention smoking composition is subjected to normal smoking conditions such as with cigarettes, the sclaral ether additive volatilizes and contributes improved flavor and aroma to the mainstream and sidestream smoke of the cigarette.

The present invention sclaral ether compounds are easily prepared and purified, and are soluble in organic solvents. The sclaral ethers are stable compounds at ambient temperatures.

Preparation Of Sclaral Ethers

Another embodiment of the present invention provides a class of sclaral ethers corresponding to the formula:

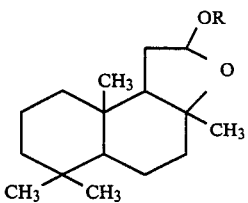

where R is an alkyl group containing between about 1–4 carbon atoms.

The sclaral ethers corresponding to the above formula are novel compounds, with the exception of sclaral methyl ether which is described in Stoll and Hinder *Helvetica Chemica Acta*, Vol. 37(6), pp. 1866–1871 (1954).

The sclaral ethers can be prepared in accordance with the following reaction scheme:

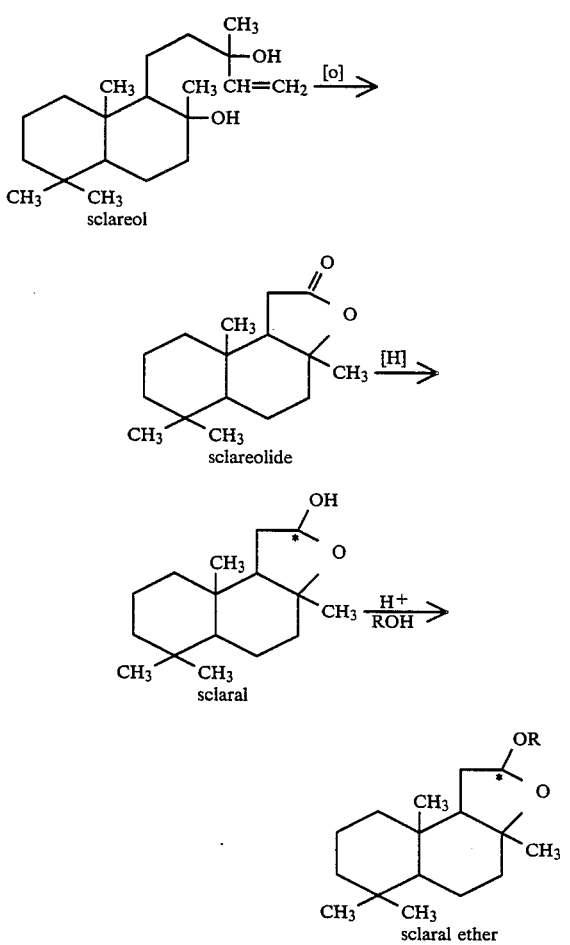

Sclareol is a natural constituent of clary sage, *Salvia sclarea*. U.S. Pat. No. 3,060,172 describes a process for isolating sclareol from clary sage.

Sclareolide is a commercial product available from several United States suppliers.

The reduction of sclareolide to sclaral introduces a new chiral center at the 2-hydroxy position in the chemical structure. The subsequent etherification of the 2-hydroxy position yields a product which is a mixture of two stereoisomers. Sclaral ether stereoisomeric mixtures can be separated chromatographically.

For purposes of application as a smoking composition flavorant additive, either the stereoisomeric mixture or the individual stereoisomers can be employed depending on the desired effect.

Preparation Of Tobacco Compositions

In a further embodiment, the present invention provides a method of preparing a smoking composition which is adapted to impart improved taste to mainstream smoke and improved aroma to sidestream smoke under smoking conditions which method comprises incorporating into natural tobacco and/or reconstituted tobacco and/or tobacco substitute between about 0.0001 and 2 weight percent, based on composition weight, of a sclaral ether flavorant additive corresponding to the formula:

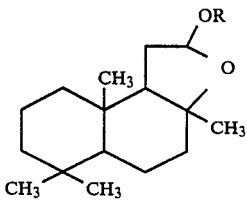

where R is an alkyl group containing between about 1–4 carbon atoms.

The invention sclaral ether flavorant additive can be incorporated into the tobacco in accordance with methods known and used in the art. Preferably the flavorant additive is dissolved in a solvent such as alcohol or aqueous alcohol and then sprayed or injected into the tobacco and/or tobacco substitute matrix. Such method ensures an even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5–5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742: and references cited therein, incorporated herein by reference.

U.S. Pat. No. 3,703,177 describes a process for preparing a non-tobacco smoking product from sugar beet pulp, which process involves the acid hydrolysis of the beet pulp to release beet pectins, and at least an alkaline earth treatment thereafter to cause crosslinking of the pectins and the formation of a binding agent for the exhausted beet matrix.

U.S. Pat. No. 3,796,222 describes a smoking product derived from coffee bean hulls. The hulls are treated with reagents that attack the alkaline earth metal crosslinks causing the release of the coffee pectins. The pectins act as a binding agent and together with the treated hulls may be handled and used similarly to a tobacco product.

U.S. Pat. No. 4,019,521 discloses a process for forming a smoking material which involves heating a cellulosic or carbohydrate material at a temperature of 150°–750° C. in an inert atmosphere for a period of time sufficient to effect a weight loss of at least 60 percent but not more than 90 percent.

U.S. Pat. No. 4,079,742 discloses a process for the manufacture of a synthetic smoking product from a cellulosic material, which process involves a pyrolysis step and a basic extraction step to yield a resultant matrix which has a tobacco-like brown color and has improved smoking characteristics.

The following Examples are further illustrative of the present invention. The specific ingredients and processing parameters are presented as being typical, and various modifications can be derived in view of the foregoing disclosure within the scope of the invention.

Example II illustrates the preparation of sclaral ether compounds in accordance with the present invention. Infrared and nuclear magnetic resonance analyses are utilized to confirm the structure of each compound.

As demonstrated in Example III, when a present invention sclaral ether is incorporated into low delivery filtered cigarette tobacco filler, there is a detectable enhancement of flavor and body in the mainstream smoke as compared to control cigarettes not containing a sclaral ether flavorant additive.

EXAMPLE I

This Example illustrates the preparation of sclaral.

A solution of 3.0 g of sclareolide (Tobacco Technology Inc., Upperco, Md.) in 100 ml of toluene is cooled to −70° C. A 12 ml quantity of 1.0 M of diisobutylaluminum hydride is added dropwise to the cooled solution over a one hour period. The reaction is quenched at −70° C. by slow addition of 30 ml of 10% sulfuric acid, and the reaction mixture is warmed to room temperature.

The organic layer is separated, and the aqueous phase of the reaction mixture is extracted with diethyl ether. The combined organic phases are washed successively with water, saturated sodium carbonate solution, water, and then saturated sodium chloride solution. After drying over sodium sulfate, the organic solvent is removed under reduced pressure to provide 3.0 g of sclaral (95% purity). Analytically pure material was obtained by liquid chromatography.

The structure of the compound is confirmed by IR and NMR spectroscopy.

EXAMPLE II

This Example illustrates the preparation of sclaral ethers in accordance with the present invention.

A. A 1.5 ml quantity of absolute ethanol and 0.01 g of p-toluene sulfonic acid are added to a solution of 136 mg of sclaral in methylene chloride. The reaction medium is stirred at room temperature for four hours to complete the etherification reaction.

The solvent is evaporated under reduced pressure to yield a residual product. The product is dissolved in diethyl ether, filtered, and after removal of the solvent a 152 mg quantity of essentially pure sclaral ethyl ether mixture of two 2-ethoxy position stereoisomers is obtained.

B. Sclaral methyl ether, sclaral isopropyl ether and sclaral t-butyl ether are prepared in the same manner as described above, except that absolute methanol, isopropanol and t-butanol, respectively, are employed as a reactant instead of ethanol.

C. A product mixture of two sclaral alkyl ether stereoisomers prepared as described above is separated into single stereoisomer fractions by means of high performance liquid chromatography (HPLC). In every case the major isomer elutes first.

HPLC Procedure

Normal phase chromatography was done on a Waters instrument and a Whatman M9® 10/50 Partisil column. The mobile phase was 2,2,4-trimethylpentane ethylacetate 95:5 or 98:2 and detection was by refractive index.

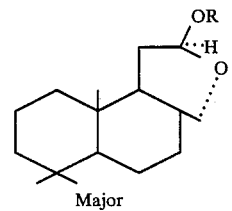

Major

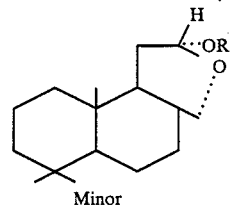

Minor

EXAMPLE III

This Example illustrates the preparation of present invention smoking compositions containing a sclaral ether flavorant additive.

Commercial low delivery filter cigarettes are treated with a sclaral ether flavorant additive as listed in the Table, by applying with a hypodermic syringe along the core of each cigarette an amount of ethanolic solution providing 0.005% of the flavorant based on the weight of the tobacco. The cigarettes are conditioned to eliminate the solvent.

The treated cigarettes and control cigarettes are smoked by a panel of experienced smokers. The results of the subjective comparative test are summarized in the Table.

TABLE

| COMPOUND | | ODOR AT ROOM TEMPERATURE | | SMOKE FLAVOR PROPERTIES |
|---|---|---|---|---|
| | | neat | *In 95% EtOH | |
| sclaral methyl ether | 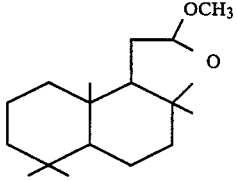 OCH₃ | major (l), very woody minor (s), none | sweet, cedar woody | sweet, low woody, peppery peppery |
| sclaral ethyl ether | 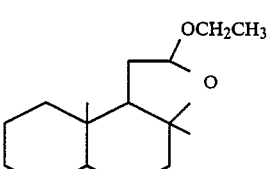 OCH₂CH₃ | major (l), slight woody minor (l), slight rancid | quite cedar woody sour | sweet, smooth, some cedar woody sweet, moderate woody, flue-cured peppery |
| sclaral isopropyl ether | 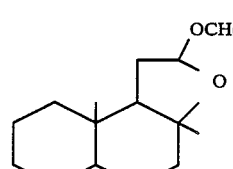 OCH(CH₂)₂ | major (s), none minor | none | smoother, rounded, well-balanced |
| sclaral t-butyl ether | 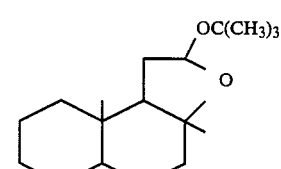 OC(CH₃)₃ | major (s), none minor (s), none | slight dry woody slight dry woody | green-bitter, smoother, slight woody |

*Sampled from solution on a perfume blotter and let sit until solvent evaporated.
(l) = liquid
(s) = solid

What is claimed is:

1. A smoking composition comprising an admixture of (1) combustible filler selected from natural tobacco, reconstituted tobacco and tobacco substitutes, and (2) between about 0.0001 and 2 weight percent, based on the total weight of filler, of a sclaral ether flavorant additive corresponding to the formula:

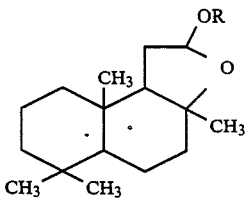

where R is an alkyl group containing between about 2–4 carbon atoms.

2. A smoking composition in accordance with claim 1 wherein the tobacco substitutes are selected from pectinaceous cellulosic and other carbohydrate materials.

3. A smoking composition in accordance with claim 1 wherein the sclaral ether additive is 2-methoxy-3a,6,6-,9a-tetramethyldodecahydronaphtho[2,1-b]furan.

4. A smoking composition in accordance with claim 1 wherein the sclaral ether additive is 2-ethoxy-3a,6,6,9a-tetramethyldodecahydronaphtho[2,1-b]furan.

5. A smoking composition in accordance with claim 1 wherein the sclaral ether additive is 2-isopropoxy-3a,6,6,9a-tetramethyldodecahydronaphtho[2,1-b]furan.

6. A smoking composition in accordance with claim 1 wherein the sclaral ether additive is 2-t-butoxy-3a,6,6-,9a-tetramethyldodecahydronaphtho[2,1-b]furan.

7. A smoking composition in accordance with claim 1 wherein the sclaral ether additive is a mixture comprising two 2-alkoxy position stereoisomers.

8. A smoking composition in accordance with claim 1 wherein the sclaral ether additive is a single 2-alkoxy position stereoisomer.

9. A method of preparing a smoking composition which is adapted to impart an improved flavor to the mainstream smoke and an improved aroma to the sidestream smoke under smoking conditions, which method comprises incorporating into natural tobacco, reconstituted tobacco or tobacco substitute between about 0.0001 and 2 weight percent, based on composition weight, of a sclaral ether flavorant additive corresponding to the formula:

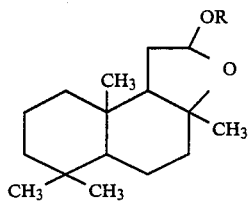
where R is an alkyl group containing between about 2-4 carbon atoms.
10. A sclaral ether corresponding to the formula:
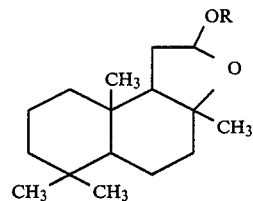
where R is an alkyl group containing between 2 and about 4 carbon atoms.
11. 2-Ethoxy-3a,6,6,9a-tetramethyldodecahydronaphtho[2,1-b]furan.
12. 2-Isopropoxy-3a,6,6,9a-tetramethyldodecahydronaphtho[2,1-b]furan.
13. 2-t-Butoxy-3a,6,6,9a-tetramethyldodecahydronaphtho[2,1-b]furan.
* * * * *